(12) United States Patent  (10) Patent No.: US 8,702,749 B2
Twomey  (45) Date of Patent: Apr. 22, 2014

(54) LEVER LATCH ASSEMBLIES FOR VESSEL SEALER AND DIVIDER

(75) Inventor: John R. Twomey, Longmont, CO (US)

(73) Assignee: Covidien LP, Mansfield, MA (US)

( * ) Notice: Subject to any disclaimer, the term of this patent is extended or adjusted under 35 U.S.C. 154(b) by 280 days.

(21) Appl. No.: 13/157,047

(22) Filed: Jun. 9, 2011

(65) Prior Publication Data

US 2012/0316601 A1 Dec. 13, 2012

(51) Int. Cl.
*A61B 17/00* (2006.01)

(52) U.S. Cl.
USPC ........................................................ 606/205

(58) Field of Classification Search
USPC ................................ 606/205–208
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,084,057 A | 1/1992 | Green et al. |
| D343,453 S | 1/1994 | Noda |
| 5,308,357 A | 5/1994 | Lichtman |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,607,436 A | 3/1997 | Pratt et al. |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| 5,935,126 A | 8/1999 | Riza |
| D416,089 S | 11/1999 | Barton et al. |
| D424,694 S | 5/2000 | Tetzlaff et al. |
| D425,201 S | 5/2000 | Tetzlaff et al. |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Gregory Anderson

(57) ABSTRACT

A surgical instrument includes a housing and an end effector spaced from the housing and transitionable between first and second conditions. A drive bar is coupled to the end effector and extends into the housing. The drive bar is translatable between first and second positions for transitioning the end effector between the first and second conditions. A handle assembly is moveable between initial and actuateds position for translating the drive bar between the first and second positions. One or more linkages couple the drive bar, the handle assembly, and the housing to one another by at least first, second and third pivots. At least one of the pivots is fixed and at least one of the pivots is floating. The second pivot is movable relative to the first and third pivots between an unlatched position and an over-center latched position for latching the end effector in the second condition.

13 Claims, 12 Drawing Sheets

(56) References Cited

U.S. PATENT DOCUMENTS

| | | | |
|---|---|---|---|
| 6,099,537 A | 8/2000 | Sugai et al. | |
| H1904 H | 10/2000 | Yates et al. | |
| 6,270,508 B1 | 8/2001 | Klieman et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| 6,923,806 B2 * | 8/2005 | Hooven et al. | 606/41 |
| D509,297 S | 9/2005 | Wells | |
| D525,361 S | 7/2006 | Hushka | |
| 7,083,618 B2 * | 8/2006 | Couture et al. | 606/51 |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| 7,789,878 B2 | 9/2010 | Dumbauld et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| 2006/0190035 A1 | 8/2006 | Hushka et al. | |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 19946527 | 12/2001 |
| DE | 10045375 | 10/2002 |
| DE | 10 2004 026 179 | 12/2005 |
| DE | 20 2007 009 165 | 10/2007 |
| DE | 20 2007 009 317 | 10/2007 |
| DE | 20 2007 016 233 | 3/2008 |
| DE | 19738457 | 1/2009 |
| DE | 10 2008 018 406 | 7/2009 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2003-245285 | 9/2003 |
| JP | 2004-517668 | 6/2004 |
| JP | 2004-528869 | 9/2004 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/876,668, filed Sep. 7, 2010, Sara E. Anderson.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.

(56) References Cited

OTHER PUBLICATIONS

U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/308,147, filed Nov. 30, 2011, E. Christopher Orton.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/337,699, filed Dec. 27, 2011, David A. Schechter.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument" ; Innovations That Work, Jun. 2003.

Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, Vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With The LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight And Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.

(56) References Cited

OTHER PUBLICATIONS

Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report Ep 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.

(56) References Cited

OTHER PUBLICATIONS

Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

LEVER LATCH ASSEMBLIES FOR VESSEL SEALER AND DIVIDER

BACKGROUND

1. Technical Field

The present disclosure relates to surgical instruments and, more particularly, to lever latch mechanisms for use with a surgical forceps for sealing and/or dividing various tissue structures.

2. Description of Related Art

Surgical forceps utilize both mechanical clamping action and electrical energy to affect hemostasis by heating the tissue and blood vessels to coagulate, cauterize and/or seal tissue. Many surgical procedures require cutting and/or ligating large blood vessels and large tissue structures. Due to the inherent spatial considerations of the surgical cavity, surgeons often have difficulty suturing vessels or performing other traditional methods of controlling bleeding, e.g., clamping and/or tying-off transected blood vessels or tissue. By utilizing an electrosurgical forceps, a surgeon can either cauterize, coagulate/desiccate and/or simply reduce or slow bleeding by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, larger vessels can be more difficult to close using these standard techniques.

In order to resolve many of the known issues described above and other issues relevant to cauterization and coagulation, a recently developed technology has been developed called vessel or tissue sealing. The process of coagulating vessels is fundamentally different than electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass with limited demarcation between opposing tissue structures. Coagulation of small vessels is sufficient to permanently close them, while larger vessels and tissue need to be sealed to assure permanent closure.

In order to effectively seal larger vessels (or tissue) two predominant mechanical parameters are accurately controlled: 1) the pressure applied to the tissue (e.g., between about 3 kg/cm$^2$ to about 16 kg/cm$^2$); and 2) the gap distance between the electrodes (e.g., between about 0.001 inches to about 0.008 inches). More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of an effective seal.

As an alternative to open electrosurgical forceps for use with open surgical procedures, many modern surgeons use endoscopes and endoscopic electrosurgical apparatus (e.g., endoscopic forceps) or laparoscopic forceps for remotely accessing organs through smaller, puncture-like incisions. As a direct result thereof, patients tend to benefit from less scarring, fewer infections, shorter hospital stays, less pain, less restriction of activity, and reduced healing time. Typically, the forceps are inserted into the patient through one or more various types of cannulas or access ports (typically having an opening that ranges from about five millimeters to about twelve millimeters) that has been made with a trocar. As such, smaller cannulas are typically more desirable relative to larger cannulas. Forceps that are configured for use with small cannulas (e.g., cannulas less than five millimeters) may present design challenges for a manufacturer of electrosurgical instruments.

SUMMARY

A surgical instrument is provided in accordance with one embodiment of the present disclosure. The surgical instrument includes a housing and an end effector assembly spaced-apart from the housing. The end effector assembly is transitionable between a first condition and a second condition. A drive bar is coupled to the end effector assembly at a first end thereof and extends therefrom into the housing. The drive bar is selectively longitudinally translatable between a first position and a second position for transitioning the end effector assembly between the first condition and the second condition. A handle assembly is also provided. The handle assembly is moveable between an initial position and an actuated position for translating the drive bar between the first position and the second position. One or more linkages couple the drive bar, the handle assembly, and the housing to one another via three or more pivots, e.g., a first pivot, a second pivot, and a third pivot. One or more of the pivots is fixed relative to the housing, and one or more of the pivots is floatable relative to the housing. The second pivot is movable relative to the first and third pivots between an unlatched position, corresponding to the initial position of the handle assembly, and an over-center latched position, corresponding to the actuated position of the handle assembly. In the over-center latched position, the end effector assembly is latched in the second condition.

In one embodiment, the end effector assembly includes a pair of jaw members. One or both of the jaw members is pivotable relative to the other between a spaced-apart position and an approximated position for grasping tissue therebetween.

In another embodiment, the drive bar is biased toward the first position such that the end effector assembly is biased toward the first condition.

In still another embodiment, a kick-out mechanism is provided. The kick-out mechanism is coupled to one of the first, second, and third pivots and is configured to release the handle assembly from the over-center latched position upon movement of the handle assembly from the actuated position to an over-actuated position. Further, the kick-out mechanism may include a piston assembly.

In yet another embodiment, one of the linkages includes a pair of driving flanges disposed on either side of the drive bar and coupled thereto such that the driving flanges urge the drive bar to translate between the first and second positions as the handle assembly is moved between the initial and actuated positions.

In still yet another embodiment, movement of the second pivot from the unlatched position to the over-center latched position produces an audible feedback signal and/or a tactile feedback signal.

In another embodiment, in the unlatched position, the second pivot is offset below the first and third pivots. When the second pivot is moved to the over-center latched position, the second pivot is offset above the first and third pivots.

In still another embodiment, in the unlatched position, the second pivot is positioned proximally of the first and third pivots. When the second pivot is moved to the over-center latched position, the second pivot is positioned distally of the first and third pivots.

A method of operating a surgical instrument is also provided in accordance with the present disclosure. The method includes providing a surgical instrument according to any of the embodiments above, or any other similar suitable surgical instrument. The method further includes moving the handle assembly from an initial position to an actuated position such that the drive bar is translated longitudinally to transition the end effector assembly from a first condition to a second condition. Upon movement of the handle assembly from the initial position to the actuated position, the second pivot is moved relative to the first and third pivots from an unlatched position to an over-center latched position to latch the end effector assembly in the second condition.

In one embodiment, the method further includes urging the handle assembly from the actuated position back to the initial position to unlatch the handle assembly and return the end effector assembly to the first condition.

In another embodiment, the method further includes moving the handle assembly from the actuated position to an over-actuated position to unlatch the handle assembly and return the end effector assembly to the first condition.

In yet another embodiment, a kick-out mechanism for urging the handle assembly back toward the initial position upon movement of the handle assembly from the actuated position to the over-actuated position is provided.

BRIEF DESCRIPTION OF THE DRAWINGS

Various embodiments of the subject instrument are described herein with reference to the drawings wherein.

DETAILED DESCRIPTION

Figure 1:
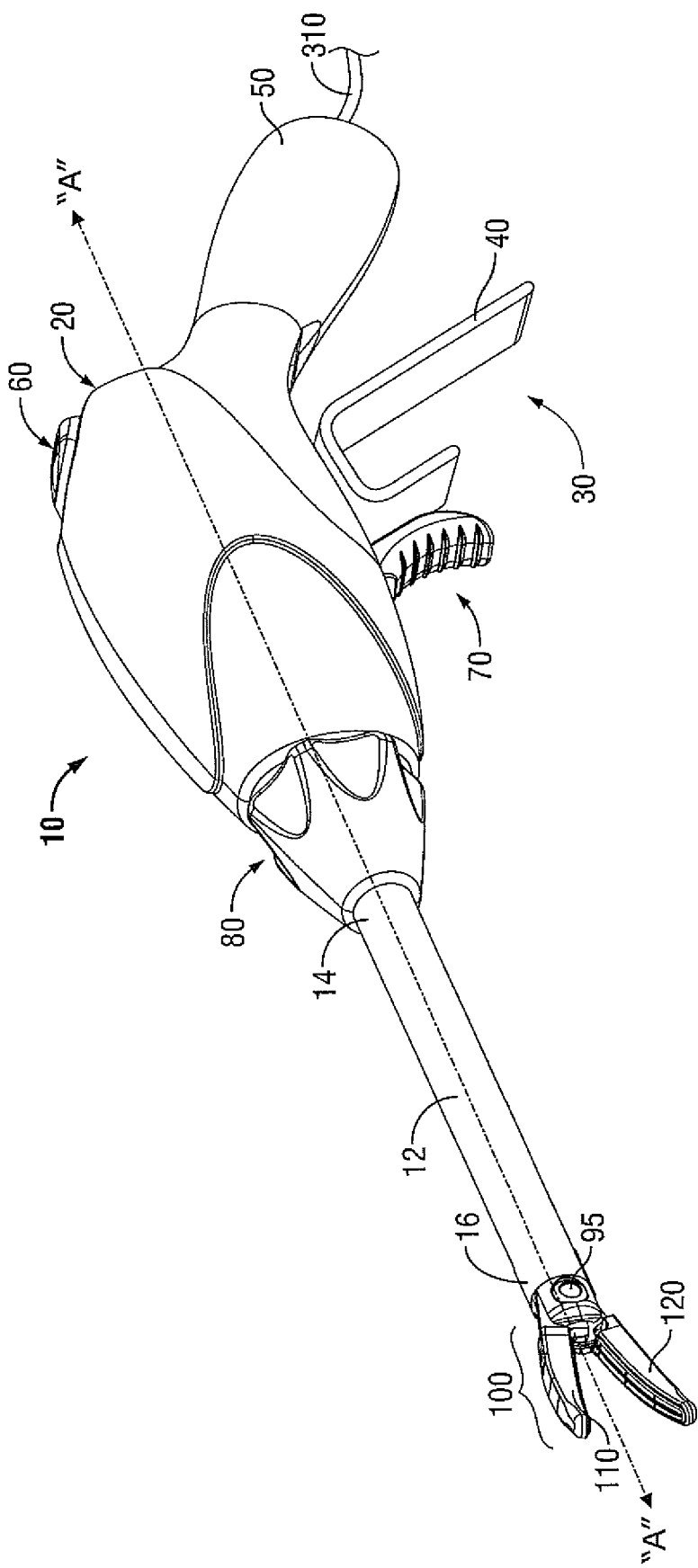
FIG. 1 is a perspective view of one embodiment of a forceps provided in accordance with the present disclosure, wherein an end effector assembly of the forceps is disposed in a spaced-apart position.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

FIGS. 1-8B show in detail the operating features and inter-cooperating components of a surgical instrument provided in accordance with the present disclosure. More specifically, the surgical instrument is shown as a forceps 10, although the present disclosure is equally applicable for use with any surgical instrument having a handle assembly operable to control and/or manipulate an end effector assembly of the surgical instrument. For the purposes herein, forceps 10 is generally described.

Forceps 10 is configured for use in various surgical procedures and includes a housing 20, a handle assembly 30, a rotating assembly 80, a trigger assembly 70, a switch 60 and an end effector assembly 100 which mutually cooperate to grasp, seal and divide tubular vessels and vascular tissues. Forceps 10 includes a shaft 12 which has a distal end 16 dimensioned to mechanically engage end effector assembly 100 and a proximal end 14 that mechanically engages housing 20. Details of how shaft 12 connects to end effector 100 are described in more detail below. The proximal end 14 of shaft 12 is received within housing 20 and the connections relating thereto are also described in detail below.

Figure 2:
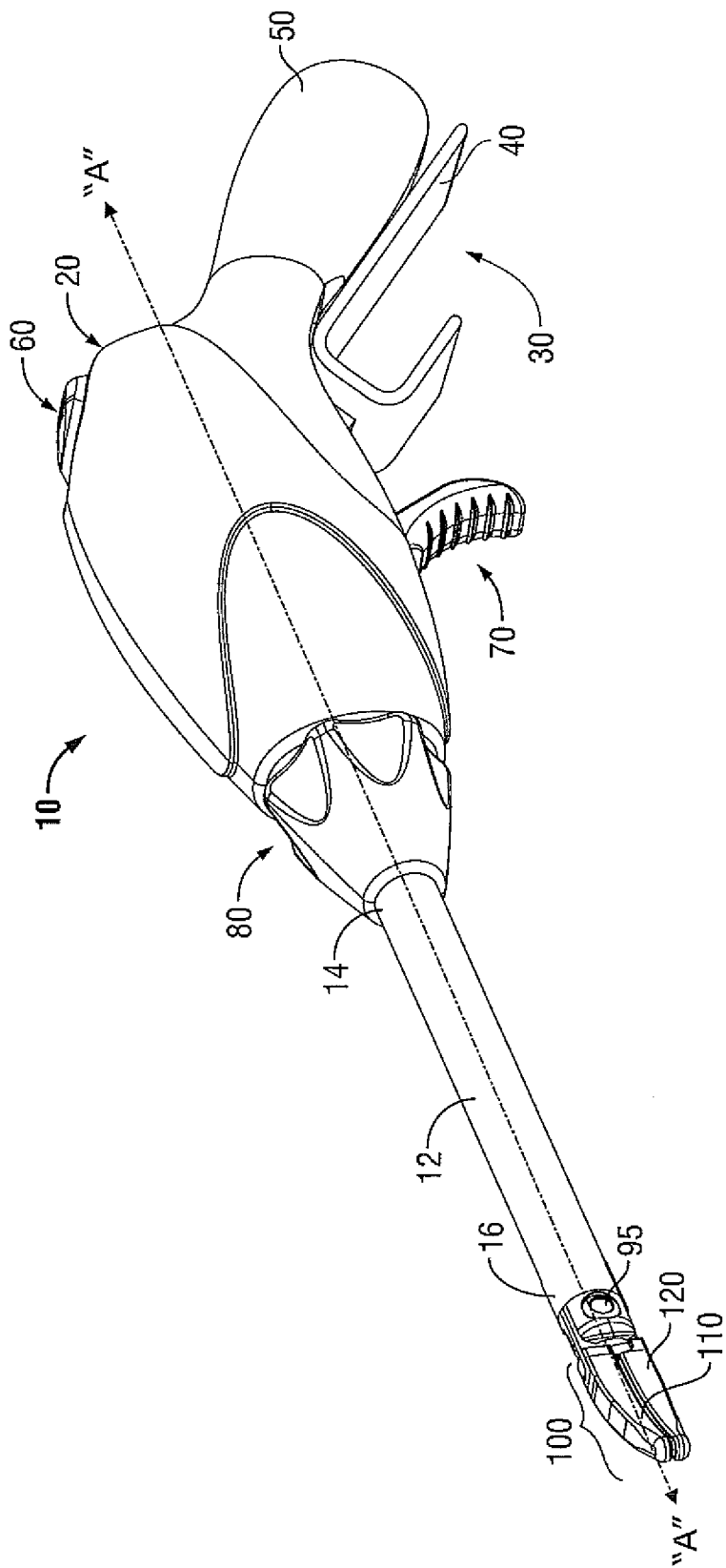
FIG. 2 is a perspective view of the forceps of FIG. 1, wherein the end effector is disposed in an approximated position.

As best seen in FIGS. 1-2, forceps 10 also includes an electrosurgical cable 310 that connects forceps 10 to an electrosurgical generator (not shown) such that upon activation of switch 60 energy is supplied to end effector assembly 100 to energize tissue disposed therein. Alternatively, forceps 10 may be configured as a battery-powered instrument. In fact, the presently disclosed handle assemblies are particularly suited for use with battery-powered instruments, or instruments containing, for example, a generator, battery, and/or control circuitry disposed within housing 20 in that the handle assemblies described herein take up minimal space within housing 20 without sacrificing mechanical advantage or limiting the latching ability thereof.

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10. Rotating assembly 80 is operatively associated with the housing 20 and is rotatable about a longitudinal axis "A-A" to rotate end effector assembly 100 about longitudinal axis "A-A."

End effector assembly 100 is attached at the distal end 16 of shaft 12 and includes a pair of opposing jaw members 110 and 120. Movable handle 40 of handle assembly 30 is ultimately connected to a drive assembly (e.g., drive assembly 230 (FIGS. 5A-5B)) to impart movement of jaw members 110 and 120 from a spaced-apart position (FIG. 1), wherein jaw members 110 and 120 are disposed in spaced relation relative to one another, to an approximated position (FIG. 2), wherein jaw members 110 and 120 cooperate to grasp tissue therebetween. End effector assembly 100 is designed as a bilateral assembly, i.e., both jaw members 110 and 120 pivot relative to one another about a pivot pin 95, although end effector assembly 100 may alternatively be configured as a unilateral end effector assembly 100. Further, jaw members 110 and 120 of end effector assembly 100 are curved to facilitate manipulation of tissue and to provide better "line of sight" for accessing targeted tissues, although other configurations may also be provided.

Figure 3:
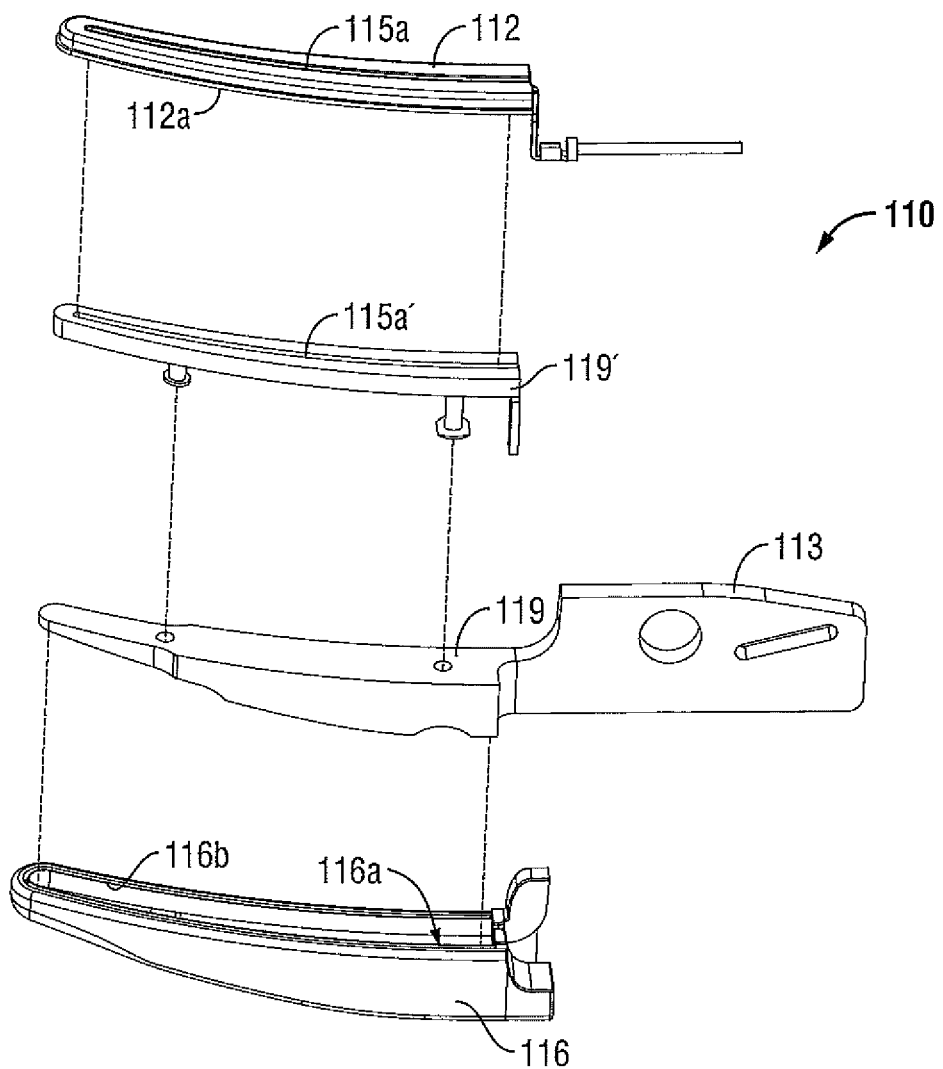
FIG. 3 is an enlarged, top perspective view of a top jaw member of the end effector assembly of FIG. 1 shown with parts separated.
Figure 4:
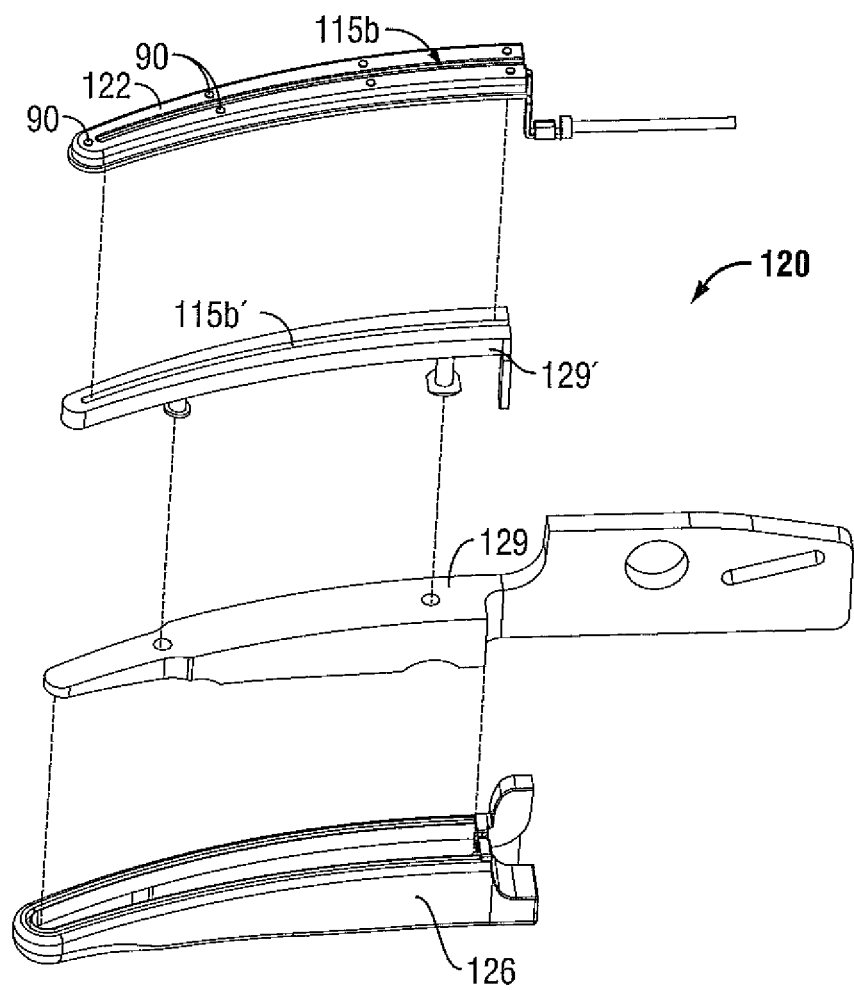
FIG. 4 is an enlarged, top perspective view of a bottom jaw member of the end effector assembly of FIG. 1 shown with parts separated.

Referring now to FIGS. 3-4, as mentioned above, end effector assembly 100 includes opposing jaw members 110 and 120 that cooperate to effectively grasp tissue for sealing purposes. Jaw member 110 includes a support base 119 that extends distally from flange 113 and that is dimensioned to support an insulative plate 119' thereon. Insulative plate 119' supports an electrically conductive sealing plate 112 thereon. Support base 119 (together with the insulative plate 119') and electrically conductive sealing plate 112 are encapsulated by an outer insulative housing 116. Outer housing 116 includes a cavity 116a that securely engages the electrically conductive sealing plate 112 as well as the support base 119 and insulative plate 119'. The electrically conductive sealing plate 112 includes a seating or retaining flange 112a that securely seats sealing plate 112 within the housing 116.

Sealing plate 112 and the outer housing 116, when assembled, form a longitudinally-oriented slot 115a defined therethrough for reciprocation of a knife blade (not shown). Insulator plate 119' similarly includes a longitudinally-oriented knife slot 115a' defined therethrough for reciprocation of the knife blade (not shown). Knife slot 115a cooperates with a corresponding knife slot 115b defined in jaw member 120 to facilitate longitudinal extension of the knife blade (not shown) along a preferred cutting plane to effectively and accurately separate the tissue when jaw members 110, 120 are disposed in the approximated position.

Jaw member 120 includes similar elements to jaw member 110 such as jaw housing 126 which encapsulates a support plate 129, an insulator plate 129' and sealing plate 122. Likewise, the electrically conductive surface or sealing plate 122 and the insulator plate 129' include respective longitudinally-oriented knife slots 115b and 115b' defined therethrough for reciprocation of the knife blade (not shown). When the jaw members 110 and 120 are closed about tissue, knife slots 115a and 115b form a complete knife channel 115 to allow longitudinal extension of the knife (not shown) in a distal fashion to sever tissue along a tissue seal. Jaw member 120 is further configured and assembled in a similar manner as described above with respect to jaw member 110.

With reference now to FIG. 4, jaw member 120 includes a series of stop members 90 disposed on the inner facing surface of the electrically conductive sealing surface 122 to facilitate gripping and manipulation of tissue and to define a gap between opposing jaw members 110 and 120 during sealing and cutting of tissue. The series of stop members 90 are applied onto sealing plate 122 during manufacturing. However, stop members 90 may additionally, or alternatively be disposed on jaw member 110.

Referring to FIGS. 3-4, in conjunction with FIGS. 1-2, jaw members 110 and 120 are engaged to the end of rotating shaft 12 by pivot pin 95 such that rotation of the rotating assembly 80 correspondingly rotates shaft 12 which, in turn, rotates end effector assembly 100. The distal end of rotating shaft 12 is bifurcated to define a channel therein for receiving jaw members 110 and 120. Pivot 95 is sizeable to provide adequate pivot strength to permit smooth and continuous pivoting of jaw members 110, 120 from the spaced-apart position (FIG. 1) to the approximated position (FIG. 2).

Several embodiments of handle assemblies configured for use with forceps 10, or any other suitable surgical instrument, are described herein with reference to FIGS. 5A-8B. As will be described below, the handle assemblies disclosed herein minimize the amount of space that the handle assembly takes up within housing 20 while still providing maximum mechanical advantage during approximation of jaw members 110, 120 and latching thereof.

Figure 5A:
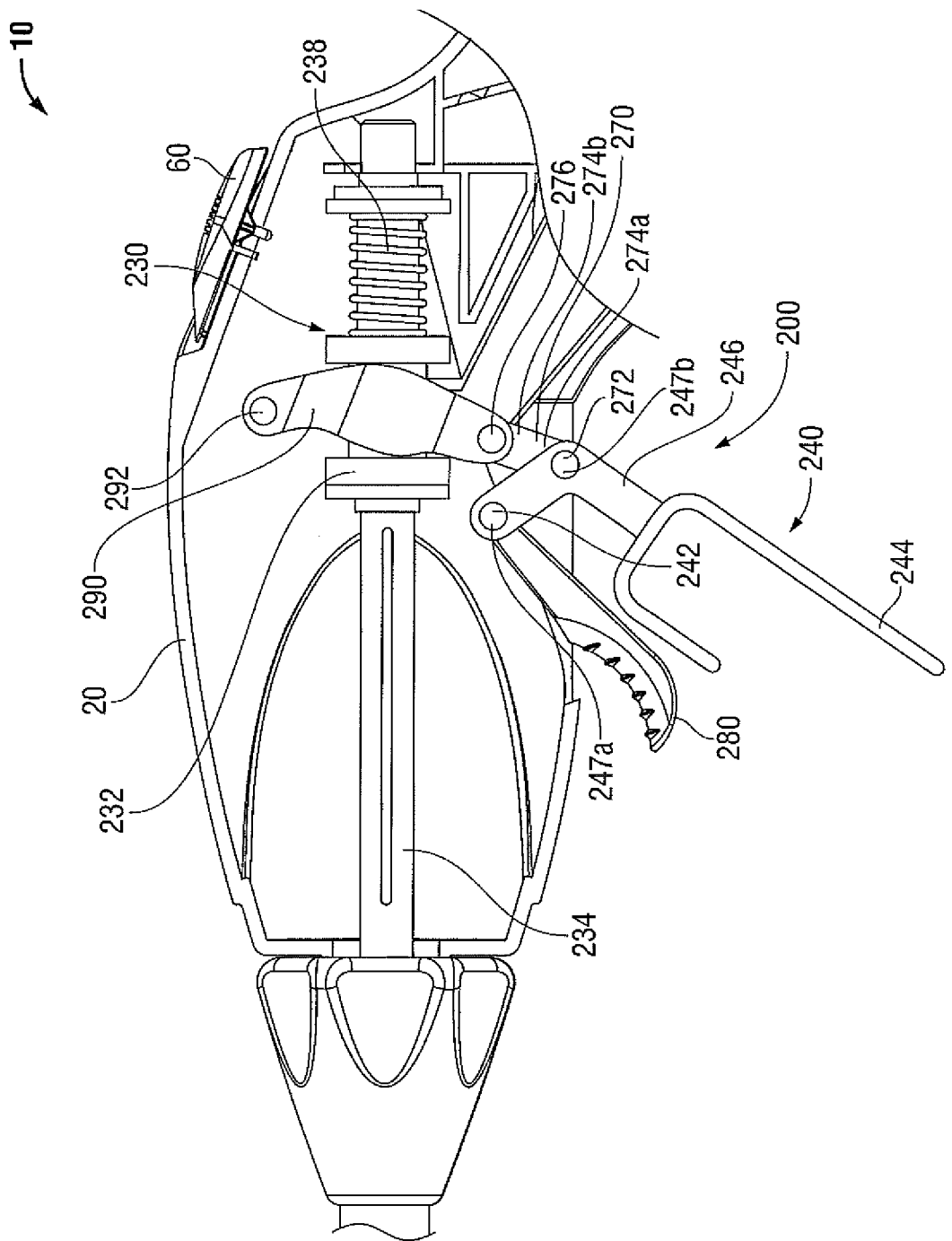
FIG. 5A is an internal, side view of one embodiment of a handle assembly configured for use with the forceps of FIG. 1, wherein a handle of the handle assembly is disposed in a first position.
Figure 5B:
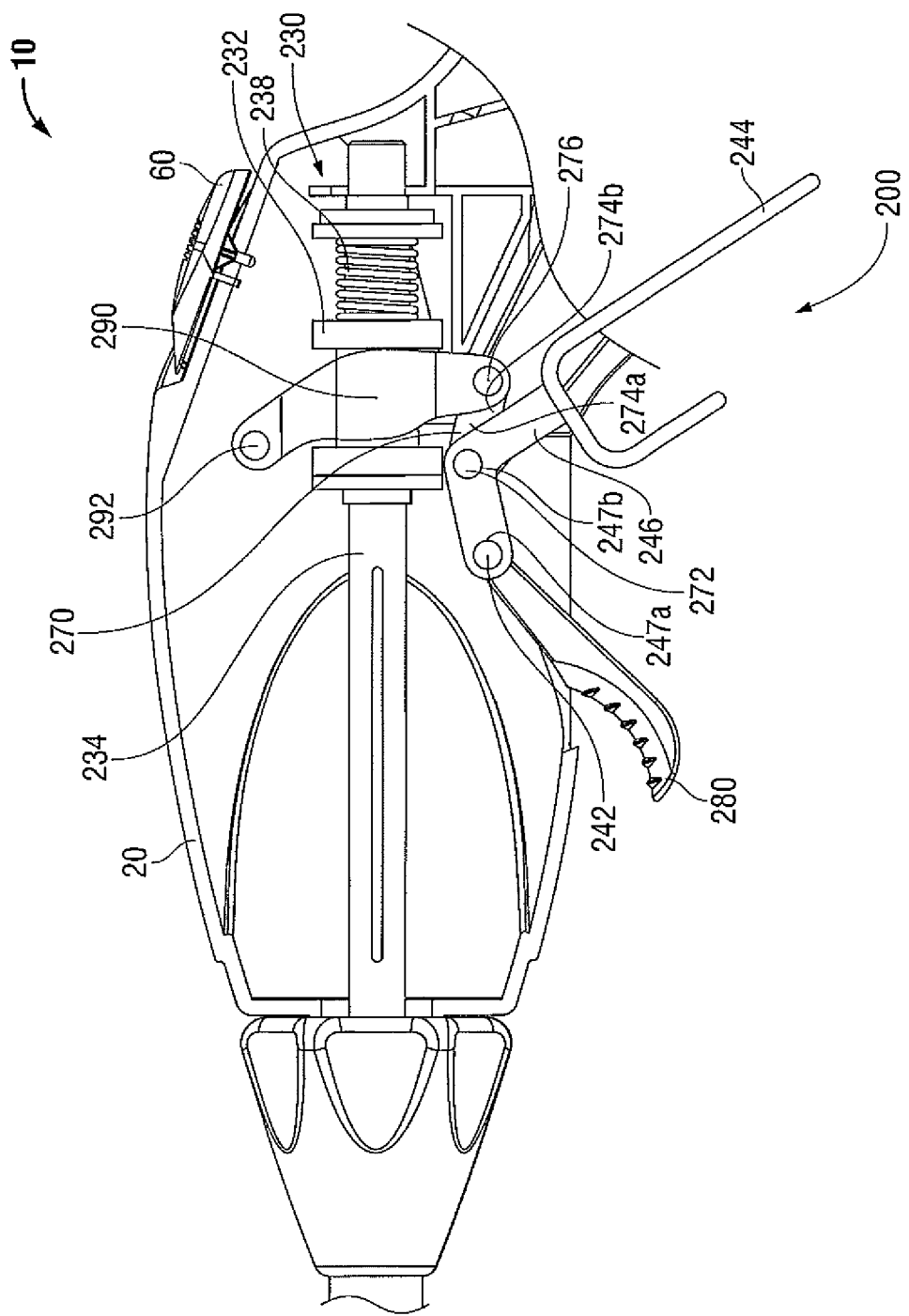
FIG. 5B is an internal, side view of the handle assembly of FIG. 5A, wherein the handle is disposed in a second position.

Referring now to FIGS. 5A and 5B, one embodiment of a handle assembly configured for use with forceps 10 is shown generally identified by reference numeral 200. Handle assembly 200 includes a moveable handle 240 that is selectively movable between an initial position, as shown in FIG. 5A, wherein moveable handle 240 is spaced-apart relative to fixed handle 50 (FIG. 1), and an actuated position, as shown in FIG. 5B, wherein moveable handle 240 is disposed in closer proximity to fixed handle 50 (FIG. 1), to impart movement of jaw members 110, 120 (FIGS. 1-2) relative to one another between the spaced-apart and approximated positions.

With continued reference to FIGS. 5A-5B, movable handle 240 includes a lever 244 that extends downwardly from housing 20 to permit grasping and manipulation of moveable handle 240 by a hand of the user. Moveable handle 240 further includes a bi-furcated arm 246 extending upwardly from lever 244 and into housing 20. Arm 246 may include first and second spaced-apart flanges, thus defining the bi-furcated configuration and may be generally L-shaped, as shown in FIGS. 5A-5B. Arm 246 also includes first and second pivotal connections 247a, 247b, respectively. More specifically, arm 246 is pivotably coupled to housing 20 at first pivotal connection 247a via fixed pivot pin 242 to permit movable handle 240 to pivot between the initial and actuated positions. Trigger 280 may likewise be pivotably coupled to housing 20 via first fixed pivot pin 242 and, thus, may also be pivotably coupled to arm 246 at first pivotal connection 247a thereof. Trigger 280 is selectively depressible to advance a knife (not shown) between jaw members 110, 120 (FIG. 1) to cut tissue grasped therebetween. A more detailed discussion of a trigger assembly configured for use with forceps 10 can be found in U.S. Pat. No. 7,857,812 to Dycus et al.

Arm 246 of moveable handle 240 is further coupled, at second pivotal connection 247b thereof, to a two-point linkage member 270 via first floating pivot pin 272. Two-point linkage 270 is coupled to first floating pivot pin 272 at first end 274a thereof and to a pair of driving flanges 290 at second end 274b by second floating pivot pin 276. Driving flanges 290, in turn, extends upwardly within housing 20, on either side of drive assembly 230, ultimately pivotably coupling to housing 20 via second fixed pivot pin 292. More specifically, driving flanges 290 are received within mandrel 232 of drive assembly 230, which is disposed about drive bar 234. Mandrel 232 retains driving flanges 290 in fixed longitudinal position relative thereto, such that pivoting of driving flanges 290 effects longitudinal translation of mandrel 232 and, thus, drive bar 234. Drive bar 234 of drive assembly 230, in turn, is longitudinally translatable between a distal position and a proximal position to effect movement of jaw members 110, 120 (FIG. 1-2) between the spaced-apart and approximated positions. Thus, upon pivoting of moveable handle 140 between the initial position (FIG. 5A) and the actuated position (FIG. 5B), driving flanges 290 are pivoted about second fixed pivot pin 292, thereby urging mandrel 232 and drive bar 234 to translate longitudinally along longitudinal axis "A-A" to pivot jaw members 110, 120 (FIGS. 1-2) between the spaced-apart and approximated positions. Drive bar 234 of drive assembly 230 may further be biased toward the distal position via spring 238, thus biasing jaw members 110, 120 (FIG. 1) toward the spaced-apart position and biasing moveable handle 240 toward the initial position.

Continuing with reference to FIGS. 5A-5B, in conjunction with FIGS. 1-2, the use and operation of handle assembly 200 will be described. Initially, drive bar 234 of drive assembly 230 is disposed in the distal position under the bias of spring 238 such that jaw members 110, 120 (FIG. 1) are disposed in the spaced-apart position and such that moveable handle 240 is disposed in the initial position. In this position, as shown in FIG. 5A, first floating pivot pin 272 is disposed below both fixed pivot pin 242 and second floating pivot pin 276.

In use, end effector assembly 100 is positioned such that tissue to be grasped, sealed, and/or divided is disposed between jaw members 110, 120. Next, moveable handle 240 is moved from the initial position to the actuated position to move jaw members 110, 120 to the approximated position to grasp tissue therebetween. More particularly, as moveable handle 240 is moved from the initial position (FIG. 5A) to the actuated position (FIG. 5B), two-point linkage 270 is pivoted about first floating pivot 272 at first end 274a thereof and is translated proximally, thereby urging second floating pivot pin 276, at second end 274b of two-point linkage 270 proximally as well. Since second floating pivot pin 276 is coupled to driving flanges 290, proximal urging of second floating pivot pin 276 similarly causes driving flanges 290 to pivot proximally about second fixed pivot pin 292, translating mandrel 232 and drive bar 234 proximally against the bias of spring 238 to move jaw members 110, 120 to the approximated position.

As shown in FIG. 5B, when moveable handle 240 is moved to the actuated position to move jaw members 110, 120 (FIG. 1) to the approximated position to grasp tissue between sealing plates 112, 122, respectively, thereof, first floating pivot pin 272 is positioned above both first fixed pivot pin 242 and second floating pivot pin 276. When this "over-center" configuration of pivot pin 272 relative to pivot pins 242 and 276 is achieved, moveable handle 240 is latched in the actuated position and, thus, jaw members 110, 120 are latched in the approximated position in that the biasing force of spring 238 is insufficient to overcome the "over-center" configuration, thereby retaining moveable handle 240 in the actuated position, drive bar 234 in the proximal position, and jaw members 110,120 (FIG. 1) in the approximated position. Further, upon achieving this "over-center" latch configuration, an audible and/or tactile "snap" may be produced, indicating to the user that the linkage has assumed this "over-center" configuration and is thus latched in position. However, if it is only desired to approximate jaw members 110, 120 without latching jaw members 110, 120 in the approximated position, moveable handle 240 is moved from the initial position toward the actuated position with insufficient force to "snap" handle assembly 230 into the "over-center" latched position.

As can be appreciated, with the linkages latched in position, the user may release moveable handle 240 although the jaw members 110, 120 are maintained in the approximated position. Further, in this configuration, the closure force imparted to sealing plates 112, 122 of jaw members 110, 120, respectively, and the gap distance between respective sealing plates 112, 122 of jaw members 110, 120 remains accurate and consistent, without the need for additional latch components or locking assemblies.

With tissue grasped between jaw members 110 and 120, forceps 10 is ready for selective application of electrosurgical energy, e.g., via activation of switch 60. By controlling the intensity, frequency and duration of the electrosurgical energy and pressure applied to the tissue, the user can effectively seal tissue. As mentioned above, in the latched position, the pressure applied to tissue is maintained substantially constant, thus helping to ensure formation of an effective tissue seal. Once tissue has been effectively sealed, the user may advance the knife (not shown) between jaw members 110, 120 to divide tissue along the previously-formed tissue seal, e.g., by depressing trigger 280.

In order to release handle assembly 200 from the latched position, moveable handle 240 is urged distally from the actuated position back toward the initial position. More specifically, moveable handle 240 is urged distally with sufficient force to move first floating pivot pin 272 back from the "over-center" position to the unlatched position, wherein first floating pivot pin 272 is positioned below first fixed pivot pin 242 and second floating pivot pin 276, thus releasing handle assembly 200 and allowing drive bar 234 to return to the distal position, jaw members 110, 120 to return to the spaced-apart position, and moveable handle 240 to return to the initial position all under the bias of spring 238. An audible and/or tactile "snap" may be produced, upon release of handle assembly 200 from the "over-center" configuration, indicating to the user that the linkage has returned to the unlatched condition.

Figure 6A:
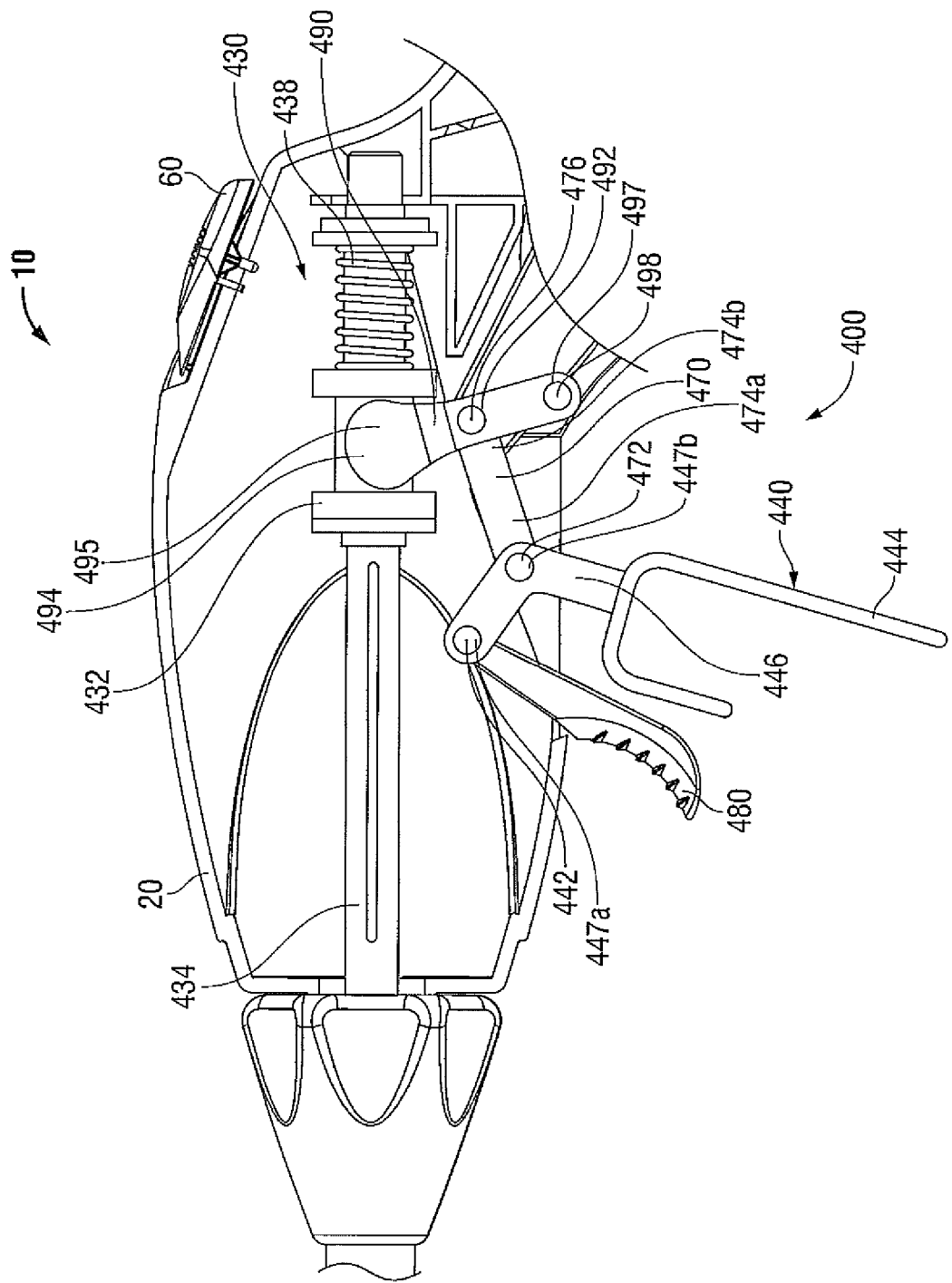
FIG. 6A is an internal, side view of another embodiment of a handle assembly configured for use with the forceps of FIG. 1, wherein a handle of the handle assembly is disposed in a first position.
Figure 6B:
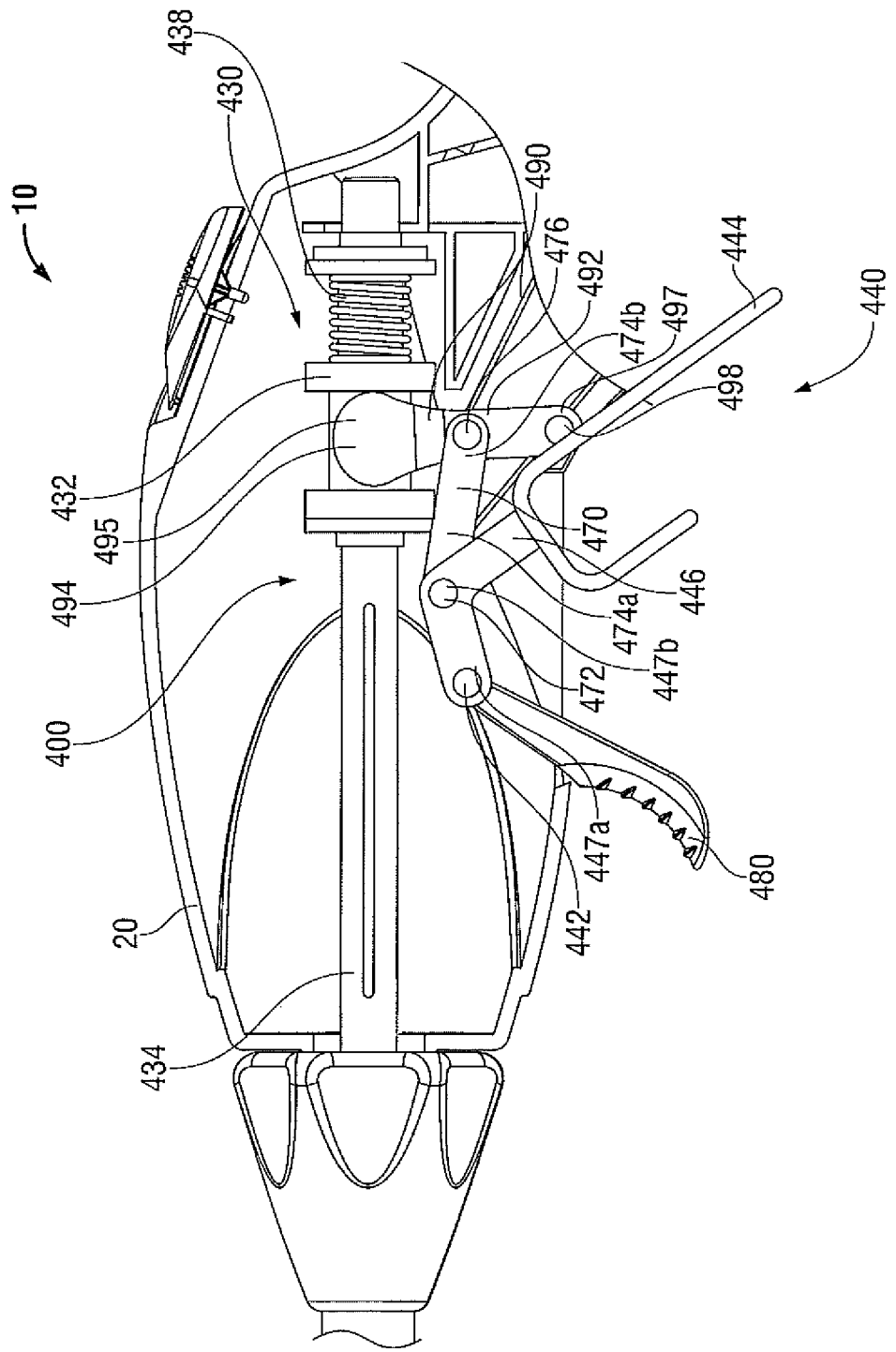
FIG. 6B is an internal, side view of the handle assembly of FIG. 6A, wherein the handle is disposed in a second position.

Turning now to FIGS. 6A-6B, another embodiment of a handle assembly configured for use with forceps 10 is shown generally identified by reference numeral 400. Handle assembly 400 is similar to handle assembly 200 (FIGS. 5A-5B) and includes a moveable handle 440 that is selectively movable between an initial position, as shown in FIG. 6A, wherein moveable handle 440 is spaced-apart relative to fixed handle 50 (FIG. 1), and an actuated position, as shown in FIG. 6B, wherein moveable handle 440 is disposed in closer proximity to fixed handle 50 (FIG. 1), to impart movement of jaw members 110, 120 (FIGS. 1-2) relative to one another between the spaced-apart and approximated positions. More specifically, movable handle 440 includes a downwardly-extending lever 444 that permits grasping and manipulation of moveable handle 440 by a hand of the user and a bifurcated arm 446 extending upwardly from lever 444 and into housing 20. Arm 446 may be generally L-shaped and includes first and second pivotal connections 447a, 447b, respectively. More specifically, arm 446 is pivotably coupled to housing 20 at first pivotal connection 447a via fixed pivot pin 442 to permit movable handle 440 to pivot between the initial and actuated positions. Trigger 480 may likewise be pivotably coupled to housing 20 via first fixed pivot pin 442 and, thus, may also be pivotably coupled to arm 446 at first pivotal connection 447a thereof.

Arm 446 of moveable handle 440 is further coupled, at second pivotal connection 447b thereof, to a two-point linkage member 470 via first floating pivot pin 472. Two-point linkage 470 is coupled to first floating pivot pin 472 at first end 474a thereof and to a central portion 492 of driving flanges 490 at second end 474b by second floating pivot pin 476. Driving flanges 490 each include a clevis 494 disposed at first ends 495 thereof that are received within mandrel 432 of drive assembly 430, on opposed sides thereof. Driving flanges 490 are pivotably coupled to housing 20 via second fixed pivot pin 498 at second ends 497 thereof. Mandrel 432 is disposed about drive bar 434 and retains driving flanges 490 in fixed longitudinal position relative thereto. Drive bar 434, in turn, is longitudinally translatable between a distal position and a proximal position to effect movement of jaw members 110, 120 (FIG. 1-2) between the spaced-apart and approximated positions. Thus, upon pivoting of moveable handle 440 between the initial position (FIG. 6A) and the actuated position (FIG. 6B), driving flanges 490 are pivoted about second fixed pivot pin 498, urging mandrel 432 and drive bar 434 to translate longitudinally along longitudinal axis "A-A" to pivot jaw members 110, 120 (FIGS. 1-2) between the spaced-apart and approximated positions. Drive bar 434 of drive assembly 430 may further be biased toward the distal position via spring 438, thus biasing jaw members 110, 120 (FIG. 1) toward the spaced-apart position and biasing moveable handle 440 toward the initial position.

Handle assembly 400 is similar to handle assembly 200 described above with reference to FIGS. 5A-5B except for the configuration of driving flanges 290, 490 and the positioning of second fixed pivot pins 292, 498, respectively. Accordingly the use and operation of handle assembly 400 will only be summarized herein to avoid unnecessary repetition.

In order to move jaw members 110, 120 from the spaced-apart position (FIG. 1) to the approximated position (FIG. 2), moveable handle 440 is moved from the initial position to the actuated position. More specifically, upon movement of moveable handle 440 from the initial position to the actuated position, driving flanges 490 are pivoted proximally about second fixed pivot pin 498 such that drive bar 434 is translated proximally against the bias of spring 438 to move jaw members 110, 120 to the approximated position. Further, upon movement of moveable handle 440 from the initial position to the actuated position, first floating pivot pin 472 is moved from a position below both first fixed pivot pin 442 and second floating pivot pin 476 to a position above both first fixed pivot pin 442 and second floating pivot pin 476, i.e., to an "over-center" position, latching handle assembly 400 in the actuated position and jaw members 110, 120 in the approximated position. The use and features of this "over-center" configuration described above with respect to handle assembly 200 apply similarly here and, thus, will not be repeated.

Figure 7A:
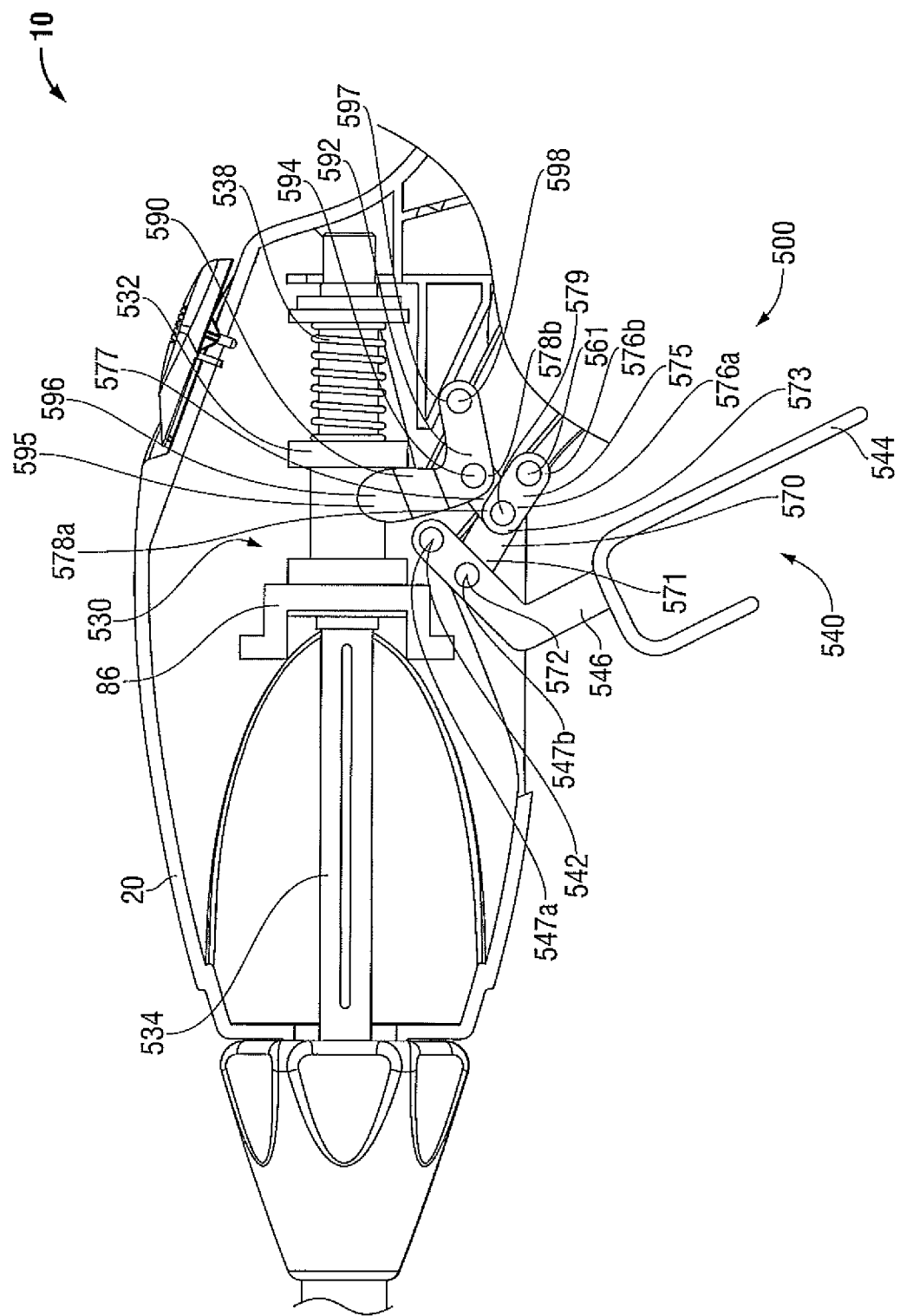
FIG. 7A is an internal, side view of still another embodiment of a handle assembly configured for use with the forceps of FIG. 1, wherein a handle of the handle assembly is disposed in a first position.
Figure 7B:
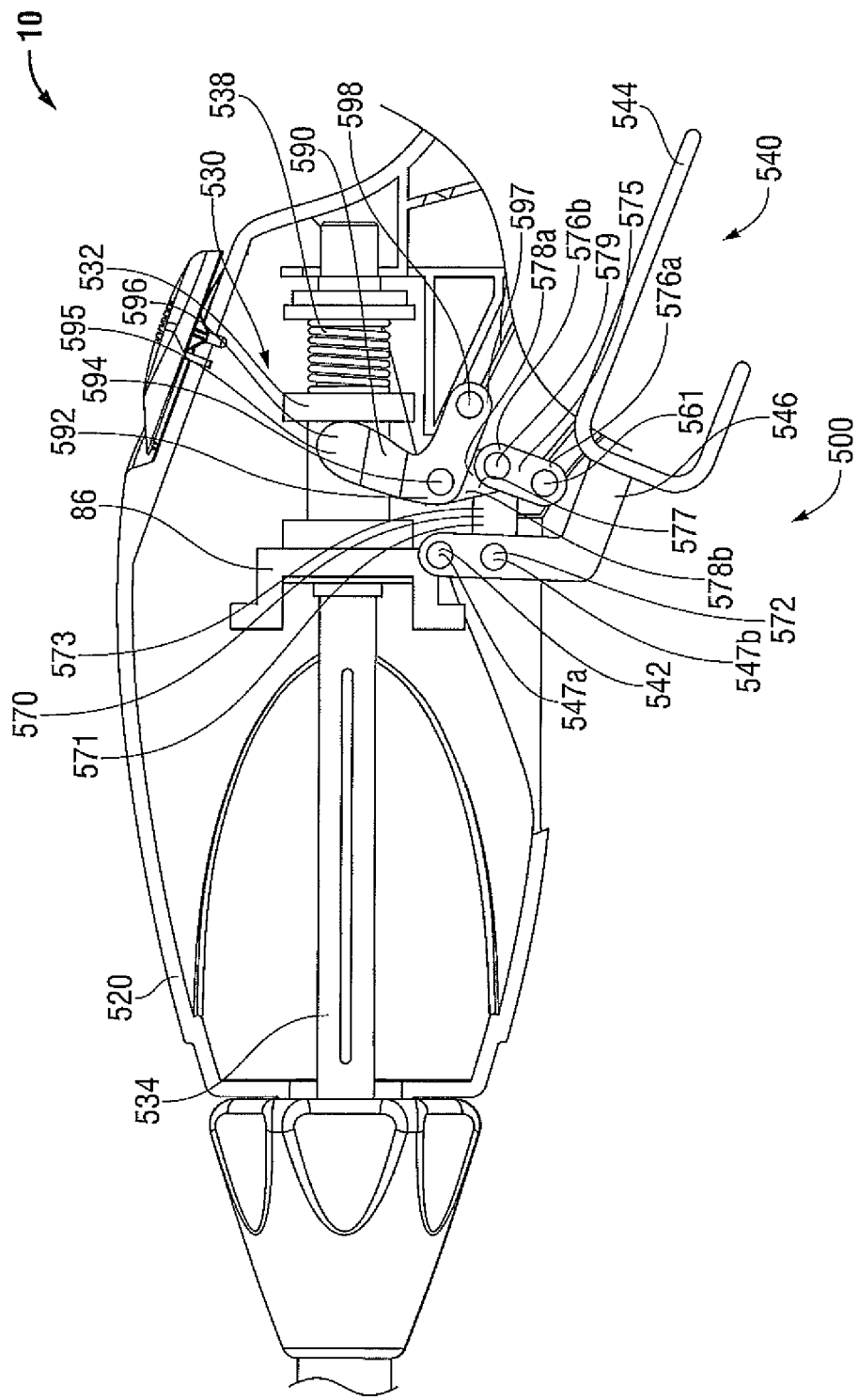
FIG. 7B is an internal, side view of the handle assembly of FIG. 7A, wherein the handle is disposed in a second position.

Referring to FIGS. 7A and 7B, another embodiment of a handle assembly, handle assembly 500, configured for use with forceps 10, is shown. Handle assembly 500 includes a moveable handle 540 that is selectively movable between an initial position, as shown in FIG. 7A, wherein moveable handle 540 is spaced-apart relative to fixed handle 50 (FIG. 1), and an actuated position, as shown in FIG. 7B, wherein moveable handle 540 is disposed in closer proximity to fixed handle 50 (FIG. 1), to impart movement of jaw members 110, 120 (FIGS. 1-2) relative to one another between the spaced-apart and approximated positions. Handle assembly 500 is advantageous in that, similar to the previous embodiments, it defines a low-profile configuration and also provides clearance within housing 20 for rotation clutch 86 of rotation assembly 80 (FIG. 1) to permit selective rotation of end effector assembly 100 (FIG. 1) about longitudinal axis "A-A" (FIG. 1).

With continued reference to FIGS. 7A-7B, movable handle 540 includes a lever 544 that extends downwardly from housing 20 to permit grasping and manipulation of moveable handle 540 by a hand of the user. Moveable handle 540 further includes a bi-furcated arm 546 extending upwardly from lever 544 and into housing 20. Arm 446 may include first and second spaced-apart flanges, thus defining the bi-furcated configuration and may be generally L-shaped. Arm 546 also includes first and second pivotal connections 547a, 547b, respectively. More specifically, arm 546 is pivotably coupled to housing 20 at first pivotal connection 547a via first fixed pivot pin 542 and to first end 571 of first two-point linkage 570 at second pivotable connection 547b thereof via first floating pivot pin 572. First two-point linkage 570, in turn, is coupled at second end 573 thereof to first ends 576a, 578a, respectively, of second and third two-point linkages 575, 577, respectively, via second floating pivot pin 579. Second end 576b of second two-point linkage 575 is coupled to housing 20 via second fixed pivot pin 561, while second end 578b of third two-point linkage 577 is coupled to the central portions 592 of driving flanges 590 via third floating pivot pin 594.

Driving flanges 590 each include a clevis 596 disposed at first end 595 thereof that are received within mandrel 532 of drive assembly 530, on opposed sides thereof. Driving flanges 590 are pivotably coupled to housing 20 via third fixed pivot pin 598 at second ends 597 thereof. Mandrel 532, as in the previous embodiments, is disposed about drive bar 534 and retains driving flanges 590 therein. Drive bar 534 is longitudinally translatable to effect movement of jaw members 110, 120 (FIG. 1-2) between the spaced-apart and approximated positions and may be biased toward a distal position via spring 538, thus biasing jaw members 110, 120 (FIG. 1) toward the spaced-apart position and biasing moveable handle 540 toward the initial position.

The use and operation of handle assembly 500 is similar to that of handle assemblies 200, 400, discussed above, and, thus, will only be summarized herein for purposes of brevity. Initially, drive bar 534 of drive assembly 530 is disposed in the distal position under the bias of spring 538 such that jaw members 110, 120 (FIG. 1) are disposed in the spaced-apart position and such that moveable handle 540 is disposed in the initial position. In this position, as shown in FIG. 7A, second floating pivot pin 579 is disposed distally of both third floating pivot pin 594 and second fixed pivot pin 561.

As moveable handle 540 is moved from the initial position (FIG. 7A) to the actuated position (FIG. 7B), the linkages are pivoted relative to one another such that driving flanges 590 are pivoted about third fixed pivot pin 598 to urge mandrel 532 and drive bar 534 proximally against the bias of spring 538 to move jaw members 110, 120 to the approximated position to grasp tissue therebetween. As shown in FIG. 7B, when moveable handle 540 is disposed in the actuated position, second floating pivot pin 579 is disposed proximally of both third floating pivot pin 594 and second fixed pivot pin 561, i.e., the "over-center" position. When this "over-center" configuration is achieved, as discussed above with respect to handle assemblies 200, 400, moveable handle 540 is latched in the actuated position and, thus, jaw members 110, 120 are latched in the approximated position. The additional features of the "over-center" configuration discussed above with regard to handle assemblies 200, 400 apply similarly to handle assembly 500 and, thus, will not be repeated.

Figure 8A:
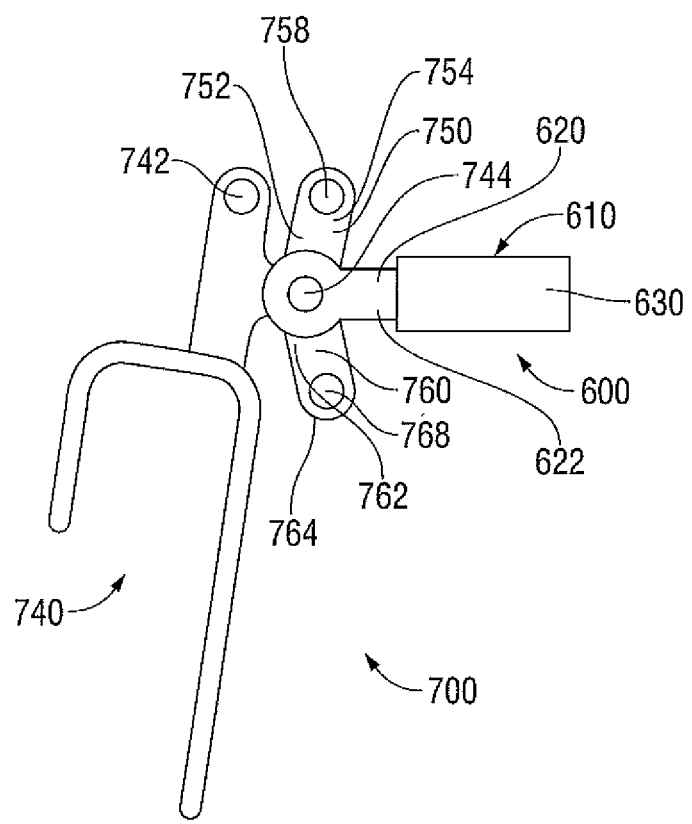
FIG. 8A is an isolated, side view of one embodiment of a kick-out mechanism for use with any of the handle assemblies above, wherein the kick-out mechanism is disposed in a first position.
Figure 8B:
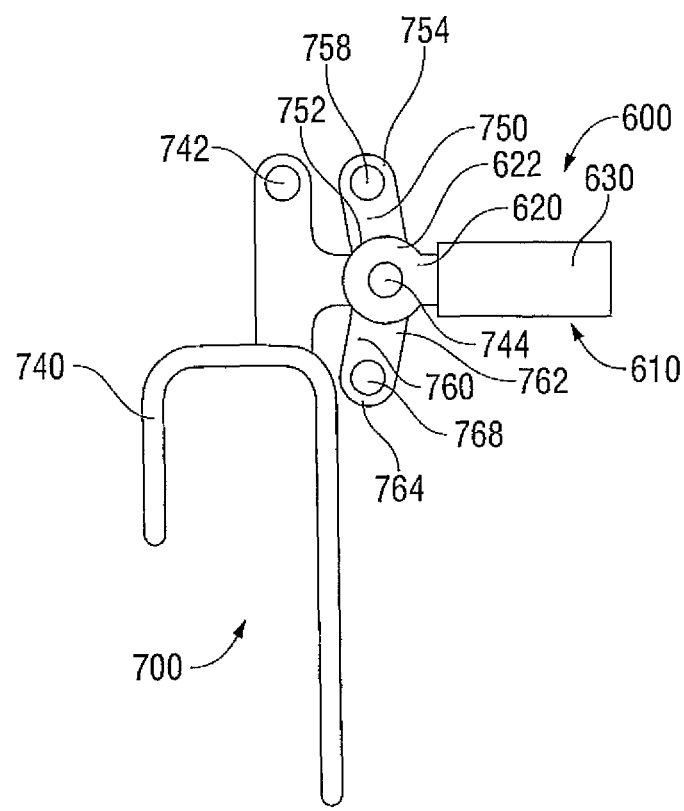
FIG. 8B is an isolated, side view of the kick-out mechanism of FIG. 8A, wherein the kick-out mechanism is disposed in a second position.

With reference now to FIGS. 8A-8B, a kick-out mechanism for use with any of the above-described handle assemblies, or any other suitable handle assembly is shown generally identified by reference numeral 600. More specifically, kick-out mechanism 600 is configured for use with an "over-center" latching mechanism, such as those discussed above with respect to handle assemblies 200, 400 and 500. Kick-out mechanism 600 is shown in use in FIGS. 8A-8B in conjunction with a handle assembly 700, similar to handle assemblies 200, 400 and 500. Handle assembly 700 includes a moveable handle 740, that is pivotably coupled to a fixed pivot pin 742 and a floating pivot pin 744. First and second linkages 750, 760, respectively, are each coupled to floating pivot pin 744 at first ends 752, 762, respectively, thereof and to respective first and second pivot pins 758, 768 at second ends 754, 764, respectively, thereof. Moveable handle 740 is moveable between an initial position, wherein floating pivot pin 744 is positioned distally of first and second pivot pins 758, 768, respectively, and an actuated position, wherein floating pivot pin 744 is disposed proximally of, or "over-center" relative to first and second pivot pins 758, 768, respectively, to move jaw members 110, 120 (FIG. 1) between the spaced-apart and approximated positions.

Kick-out mechanism 600 includes a piston assembly 610 having a piston shaft 620 that is pivotably coupled to floating pivot pin 744 at first end 622 thereof and that extends into piston housing 630. Piston shaft 620 is moveable relative to piston housing 630 between an extended position, a retracted position, and a release position, as will be described in greater detail below. Further, piston assembly 610 may be spring-loaded, or otherwise biased, to facilitate movement between these positions.

Initially, with moveable handle 640 in the initial position, wherein floating pivot pin 744 is positioned distally of first and second pivot pins 758, 768, respectively, and wherein jaw members 110, 120 (FIG. 1) are disposed in the spaced-apart position, piston assembly 610 is disposed in the extended position, as shown in FIG. 8A. When moveable handle 640 is moved to the actuated position, such that floating pivot pin 744 is moved to the "over-center" position to latch jaw members 110, 120 (FIG. 2) in the approximated position, piston assembly 610 is moved to the retracted position, as shown in FIG. 8B.

When it is desired to unlatch jaw members 110, 120 (FIG. 1), i.e., when it is desired to allow jaw members 110, 120 (FIG. 1) to return to the spaced-apart position, movable handle 640 is moved further proximally from the actuated position to an over-actuated position to move piston assembly 610 to the release position. In the release position, piston assembly 610 is loaded, or armed. Accordingly, upon release of moveable handle 640 from the over-actuated position, piston assembly 610 urges moveable handle 640, e.g., under spring, or other suitable bias, back toward the initial position with sufficient force to snap-back, or move floating pivot pin 744 from the "over-center" position back to a position distally of first and second pivots 758, 768, respectively, thereby releasing the latch and allowing jaw members 110, 120 (FIG. 1) to return to the spaced-apart position and moveable handle 640 to return to the initial position.

Put more generally, kick-out mechanism 600 serves to release handle assembly 700 from the "over-center," or latched position, upon further pulling, or depression of moveable handle 640, rather than requiring the user to manually translate moveable handle 640 distally to release the latch, thus providing a more ergonomic, spring-assisted release for handle assembly 700. As mentioned above, kick-out mechanism 600 may be employed in conjunction with any of handle assemblies 200, 400 or 500, described above, to achieve a similar result.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
    a housing;
    an end effector assembly spaced-apart from the housing and transitionable between a first condition and a second condition;
    a drive bar coupled to the end effector assembly at a first end and extending into the housing, the drive bar longitudinally translatable between a first position and a second position for transitioning the end effector assembly between the first condition and the second condition;
    a handle assembly moveable between an initial position and an actuated position for translating the drive bar between the first position and the second position; and
    at least one linkage pivotably coupling the drive bar, the handle assembly, and the housing to one another via at least a first pivot, a second pivot, and a third pivot, one of the first and third pivots fixed relative to the housing and the other of the first and third pivots floatable relative to the housing, the second pivot movable relative to the first and third pivots between an unlatched position, corresponding to the initial position of the handle assembly wherein the second pivot is disposed on a first side of a line segment connecting the first and third pivots, and an over-center latched position, corresponding to the actuated position of the handle assembly wherein the second pivot is disposed on a second, opposite side of the line segment connecting the first and third pivots to latch the end effector assembly in the second condition.

2. The surgical instrument according to claim 1, wherein the end effector assembly includes a pair of jaw members, at least one of the jaw members pivotable relative to the other between a spaced-apart position and an approximated position for grasping tissue therebetween.

3. The surgical instrument according to claim 1, wherein the drive bar is biased toward the first position such that the end effector assembly is biased toward the first condition.

4. The surgical instrument according to claim 1, further comprising a kick-out mechanism coupled to one of the first, second, and third pivots, the kick-out mechanism configured to release the handle assembly from the over-center latched position upon movement of the handle assembly from the actuated position to an over-actuated position.

5. The surgical instrument according to claim 4, wherein the kick-out mechanism includes a piston assembly.

6. The surgical instrument according to claim 1, wherein one of the linkages includes a pair of driving flanges disposed on either side of the drive bar and coupled thereto such that the driving flanges urge the drive bar to translate between the first and second positions as the handle assembly is moved between the initial and actuated positions.

7. The surgical instrument according to claim 1, wherein movement of the second pivot from the unlatched position to the over-center latched position produces at least one of an audible feedback signal and a tactile feedback signal.

8. The surgical instrument according to claim 1, wherein, in the unlatched position, the second pivot is offset below the first and third pivots and wherein, in the over-center latched position, the second pivot is offset above the first and third pivots.

9. The surgical instrument according to claim 1, wherein, in the unlatched position, the second pivot is positioned proximally of the first and third pivots and wherein, in the over-center latched position, the second pivot is positioned distally of the first and third pivots.

10. A method of operating a surgical instrument, the method comprising the steps of:
    providing a surgical instrument including:
        a housing;
        an end effector assembly spaced-apart from the housing;
        a drive bar coupled to the end effector assembly at a first end and extending into the housing;
        a handle assembly; and
        at least one linkage pivotably coupling the drive bar, the handle assembly, and the housing to one another via at least a first pivot, a second pivot, and a third pivot, one of the first and third pivots fixed relative to the housing and the other at least one of the first and third pivots floatable relative to the housing; and moving the handle assembly from an initial position to an actuated position such that the drive bar is translated longitudinally to transition the end effector assembly from a first condition to a second condition, wherein, upon movement of the handle assembly from the initial position to the actuated position, the second pivot is moved relative to the first and third pivots from an unlatched position, wherein the second pivot is disposed on a first side of a line segment connecting the first and third pivots, to an over-center latched position, wherein the second pivot is disposed on a second, opposite side of the line segment connecting the first and third pivots to latch the end effector assembly in the second condition.

11. The method according to claim 10 further comprising the step of urging the handle assembly from the actuated position back to the initial position to unlatch the handle assembly and return the end effector assembly to the first condition.

12. The method according to claim 10, further comprising the step of moving the handle assembly from the actuated position to an over-actuated position to unlatch the handle assembly and return the end effector assembly to the first condition.

13. The method according to claim 12, further comprising a kick-out mechanism for urging the handle assembly back toward the initial position upon movement of the handle assembly from the actuated position to the over-actuated position.

* * * * *